United States Patent [19]
Persson et al.

[11] 4,179,196
[45] Dec. 18, 1979

[54] COMPACT SUBJECTIVE REFRACTIVE INSTRUMENT

[75] Inventors: Staffan B. Persson, Danielson, Conn.; Robert B. Tackaberry, Williamsville, N.Y.

[73] Assignee: American Optical Corporation, Southbridge, Mass.

[21] Appl. No.: 838,178

[22] Filed: Sep. 30, 1977

[51] Int. Cl.² ............................................. A61B 3/02
[52] U.S. Cl. ........................................ 351/30; 351/36; 351/34
[58] Field of Search .................... 351/30, 36, 32, 34, 351/17

[56] References Cited
U.S. PATENT DOCUMENTS

| | | | |
|---|---|---|---|
| 3,669,530 | 6/1972 | Guyton | 351/34 |
| 4,015,889 | 4/1977 | Humphrey | 351/30 |
| 4,105,302 | 8/1978 | Tate | 351/30 X |

Primary Examiner—John K. Corbin
Assistant Examiner—Rodney B. Bovernick
Attorney, Agent, or Firm—Jeremiah J. Duggan; Alan H. Spencer; Stephen A. Schneeberger

[57] ABSTRACT

A compact ophthalmic instrument for refraction of patient's eyes is obtained by substantial folding of the optical system. The optical system is folded in one location using a reflection means that moves to vary the location of a target image being viewed by a patient for identifying the spherical power of a corrective lens, if any, required by the patient. A second folded portion of the optical system contains a cylinder means for cylindrically varying the target image.

8 Claims, 4 Drawing Figures

TEST AXIS – – – –
ALIGNMENT AXIS —·—·—
BOTH AXES —··—··—

COMPACT SUBJECTIVE REFRACTIVE INSTRUMENT

BACKGROUND OF THE INVENTION

This invention relates to a compact refractor optical system and more particularly, relates to a refractor having a test axis folded at least twice.

It is frequently desirable to position a movable member at a specified location relative to an object. One art in which such alignment is frequently practiced relates to ophthalmic instruments. Usually, ophthalmic instruments such as slit lamps, contact tonometers, and the like used the same optical system for positioning a movable portion of the instrument as that used for observing (slit lamps) or to measure (tonometers).

Subjective refractors, optometers, which present a target image for viewing by a patient are known.

U.S. Pat. No. 3,785,723 issued Jan. 15, 1974, to Guyton relates to a method of testing the eye for astigmatic error and diagrammatically describes an optical arrangement in FIG. 7. The system has a combined spherical and cylindrical unit for selective varying sphere and/or cylinder power.

U.S. Pat. No. 3,664,631 issued May 23, 1972, to Guyton further describes the sphere and cylinder lens unit, and variations thereof.

U.S. Pat. No. 3,842,254 issued Oct. 15, 1974, to Dianetti, and U.S. Pat. No. 3,832,890 issued Sept. 3, 1974, to Grolman et al, are examples of ophthalmic instruments having alignment systems in which the operator's head follows movement of the instrument during alignment.

BRIEF DESCRIPTION OF THE PRESENT INVENTION AND DRAWINGS

The present invention relates to a compact ophthalmic instrument for determining the refractive condition of a patient's eye. The subjective refractor has a test axis folded at least twice to obtain substantial compression of the instrument dimensions. Along the test axis a target image is projected to a normal image plane, the normal image plane is located at or near an eyepiece focal plane. The required amount of spherical correction is determined by moving the entire image from the normal image plane until the patient obtains optimum focus of the image. The image is cylindrically varied by a cylinder system to determine the necessary axis and cylinder power of corrective lenses required by the patient. An optical system is described in which the optical assembly has a maximum single dimension (including eyepiece) of approximately one-half the test axis distance between the target and the eyepiece, which may be conveniently located in a housing having a test axis to largest single dimension ratio of about 7:4.5.

THE PREFERRED EMBODIMENTS

Figure 1:
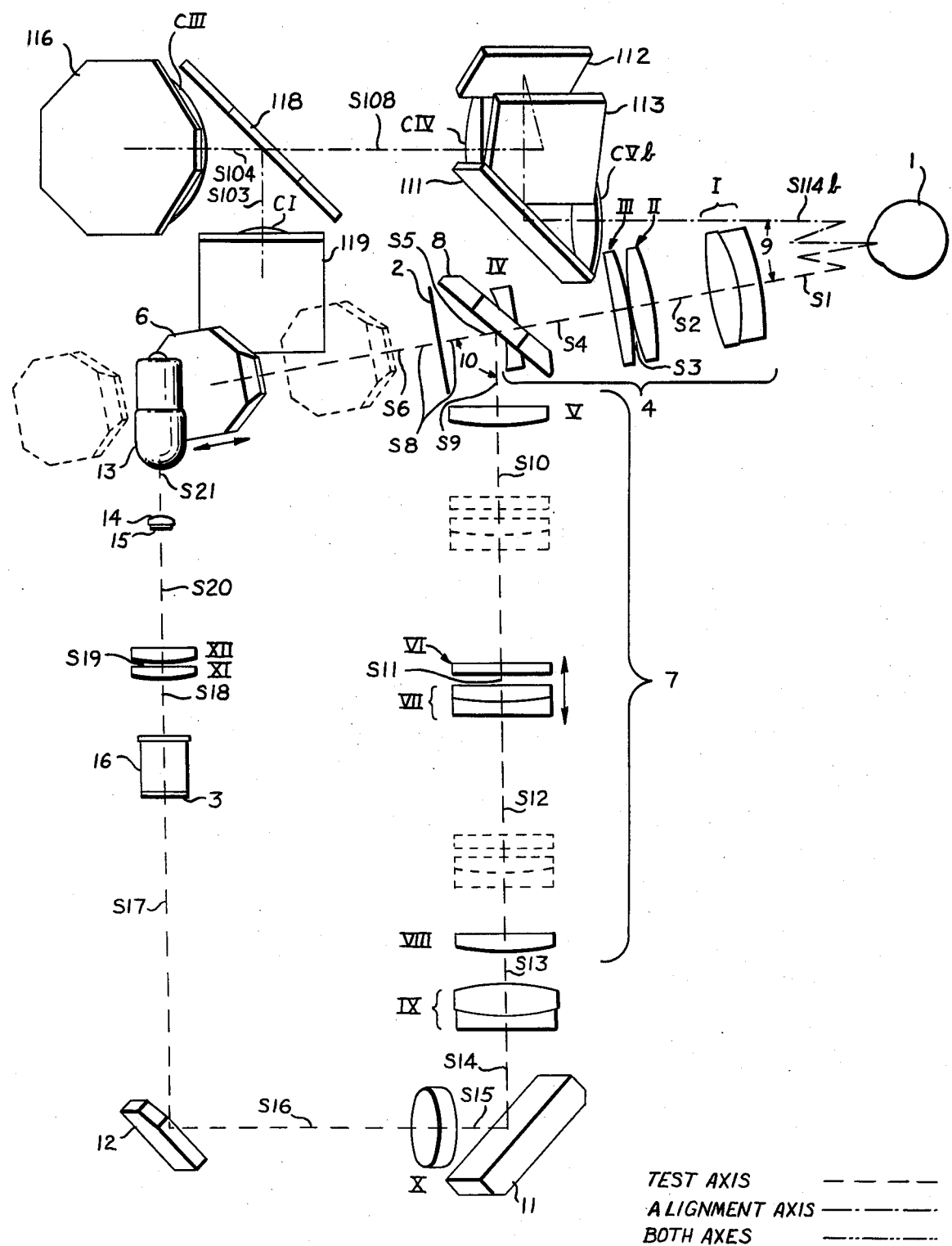
FIG. 1 is a side-view, optical diagram of the combined optometer test system and alignment system.
Figure 2:
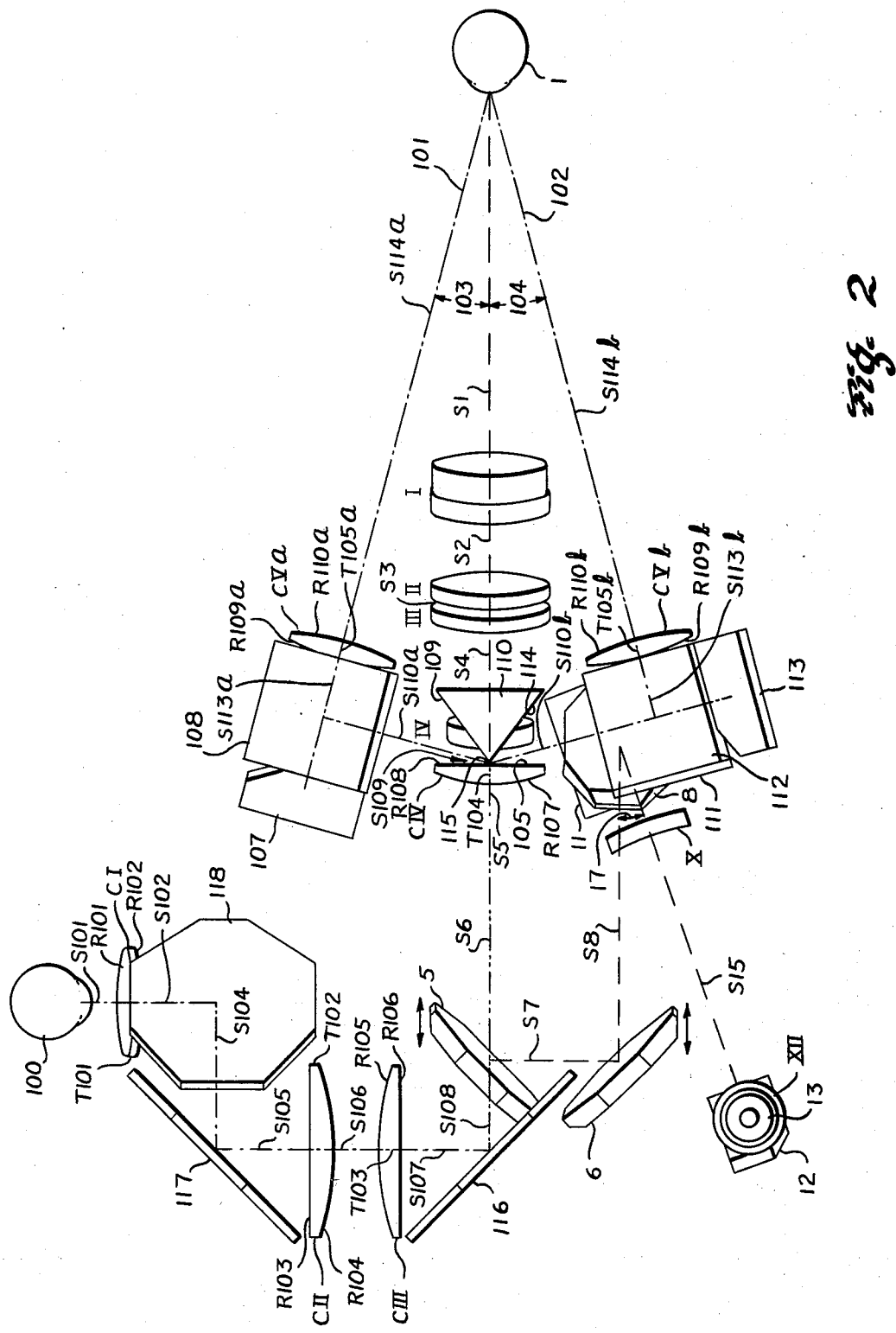
FIG. 2 is a top-view, optical diagram of the optometer and alignment systems.
Figure 3:
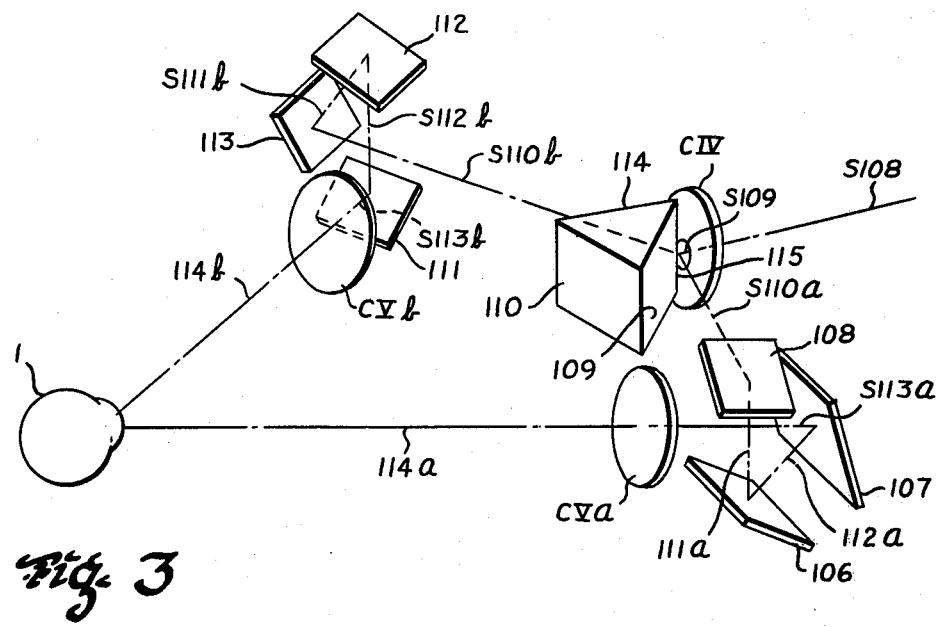
FIG. 3 is a perspective view of the range-finder, reflective-surface assemblies.

Referring to FIGS. 1 and 2, a patient having eye 1 to be tested observes an image 2 of target 3 through eyepiece 4. When the refractive condition of the patient's eye is normal, spherically and astigmatically, image 2 is in focus at the location illustrated, which corresponds to the focal plane of eyepiece 4. However, if the eye does not have normal refractive abilities, it may be necessary to move the position of image 2 along the test axis (shown as dotted line) in order to obtain proper focus for eye 1. Axial movement of image 2 is obtained by moving mirrors 5 and 6 to lengthen or shorten as necessary the optical path from target 3. Assuming no other variation in optics between mirror 6 and target 3, image 2 will be axially shifted twice the distance that mirror 5 and 6 are moved. This is highly desirable because it enables a wide range of adjustment for refractive errors, while maintaining minimum space requirements for the instrument. After the patient has adjusted the position of mirrors 5 and 6 to obtain image 2 in the best possible focus, the patient next axially rotates assembly 7 to align one of the two meridians of cylinder power with the axis of astigmatism (if any) in eye 1. Following adjustment for the best possible cylinder axis, the patient axially moves cylinder lens VI to obtain the desired power for correction of astigmatic error. The variable cylinder assembly 7 includes lenses V, VI, VII and VIII. When axially movable lens VI is centrally located, assembly 7 has a uniform power along all meridians. However, as cylinder lens VI is axially moved from its intermediate or reference position, the power of assembly 7 is changed in one meridian. The structure and operation of assembly 7 is more specifically described in co-pending application Ser. No. 705,852 filed July 16, 1976. In practice the instrument operator usually repeats the foregoing procedure, personally operating the controls to "refine" the position of mirrors 5 and 6, and frequently cylinder lens VI and/or the axial position of assembly 7.

Eyepiece 4 consists of lenses I, II, III and IV and is the subject of co-pending application Ser. No. 705,856, filed July 16, 1976, and now U.S. Pat. No. 4,066,339. The front focal plane of eyepiece 4 is located at image plane 2, which is approximately 20 mm from the concave surface of lens IV. Eye 1 is postioned 116.8 mm along the test axis from the first surface of lens I. Mirror 5 horizontally deflects the test axis 90 degrees to mirror 6, which also deflects the test axis 90 degrees along a path parallel to the portion of the test axis between eyepiece 4 and mirror 5. The test axis from the spherical system including mirrors 5 and 6 is deflected downwardly by mirror 8 in a substantially vertical direction. For convenience, the test axis between mirror 5 and eye 1 is inclined at angle 9 of about 10 degrees. Therefore, there is angle 10 of 80 degrees between the portion of the test axis extending from mirror 6 to mirror 8 and the portion of the test axis extending from mirror 8 through assembly 7. After the test axis passes through assembly 7, the axis is diverted 180 degrees by mirrors 11 and 12 into a vertical path parallel to a portion of the axis passing through assembly 7. Collimating lenses 9 and 10 cooperate with the optical system of assembly 7 to present image 2 of target 3 near the front focal plane of eyepiece 4 when mirrors 5 and 6 are in the reference position. If the reference target image is located exactly at the focal plane of eyepiece 4, the target image will appear to be at infinity. In practice, tests are generally conducted at eyecharts positioned a standard twenty feet from the patient. The preferred embodiment, therefore, has the front focal plane located 1.16 mm toward the eyepiece from the eyepiece focal plane in order to present an image appearing to be located twenty feet from the patient. Light from lamp 13 is color corrected by blue filter 14; diffused by diffuser 15 and collected by lenses XII and XI to project an image of target 3. Target 3 is mounted in a holder 16 and additional holders (not shown) may be used to hold different targets that can be selectively positionable on the test axis. The portion of the axis between mirrors 11 and 12 is preferably at angle 17 of about 20 degrees from a plane containing the portion of the axis extending from mirror 6 to mirror 11.

Collimating lenses IX and X are selected to cooperate with the optics of assembly 7 to position image 2 at the "normal" location. In the preferred embodiment the spacing between target 3 and image 2 is normally about 719 mm. The front focal length of the collimator, lenses IX and X, is about 203 mm and mirror 11 is positioned between the two lenses. Including allowances for movement of the instrument within the case with a monitoring system as hereinafter described and a supporting mechanism for the movable optical assembly, the preferred embodiment has a ratio of the optical axis length (target to eyepiece) to largest case dimension of about 7:4.5

Figure 4:
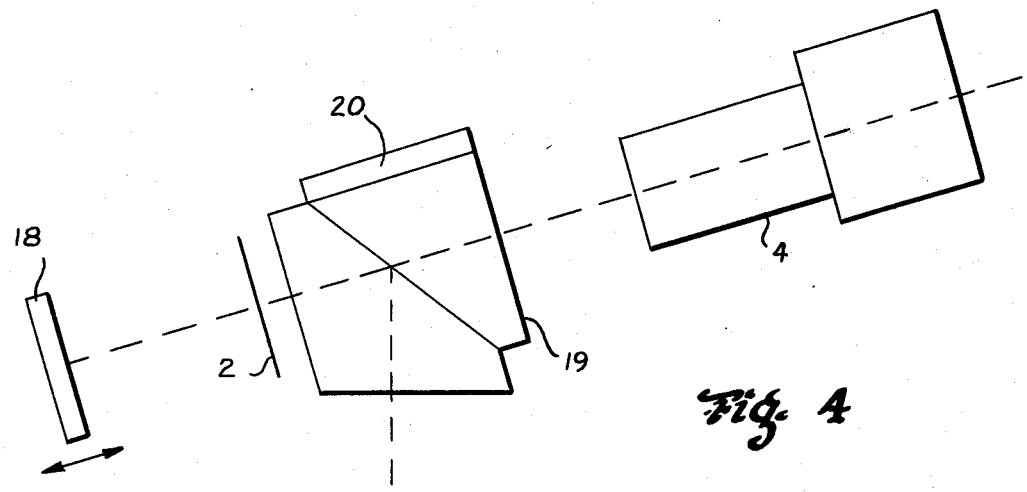
FIG. 4 is another embodiment of the variable sphere portion of the optometer test system.

Referring to FIG. 4, an alternate embodiment of the test system has an eyepiece 4 and a single mirror 18 with a beam splitter 19 positioned on the test axis therebetween. In practice, the patient looks through eyepiece 4 at image 2, which is reflected from mirror 18. Mirror 18 is moved to selectively position image 2 in the same manner as mirrors 5 and 6 are moved in the embodiment of FIG. 1. When this embodiment is used, the beam splitter acts to deflect the test axis downwardly through assembly 7 (not shown in FIG. 4) in the same manner as mirror 8 in the embodiment of FIG. 1. Light absorber 20 is cemented to the top of beam splitter 19 with an optical cement selected to minimize reflection of light from the mating surfaces of beam splitter 19 and absorber 20.

Specific parameters of a preferred optical system are set forth in Table I. The successive lens radii are designated to $R_1$ to $R_{27}$, where a minus sign (−) signifies a surface curvature having a vertex on the eye 1 side of the lens; successive axial thicknesses are designated $T_1$ to $T_{17}$; successive axial spacings from eye 1 are designated $S_1$ to $S_{21}$, and all radii thicknesses and spacings are in millimeters. The refractive indices of the successive elements are designated $ND_1$ to $ND_{15}$ and Abbe numbers of the successive elements are designated $\nu 1$ to $\nu 15$. Abbe numbers and refractive indices are absolute values.

TABLE I (Test Optics)

| Function | Lens No. | Radius (R) | Thickness (T) | Spacing (S) | Refractive Index (ND) | Abbe Number (V) |
|---|---|---|---|---|---|---|
| EYEPIECE | | | | $S_1 = \sim 116.79$ | | |
| | I | $R_1 = 134.30$ | $T_1 = 7.0$ | | $ND_1 = 1.784$ | $\nu 1 = 25.16$ |
| | | $R_2 = 50.27$ | $T_2 = 10.0$ | | $ND_2 = 1.589$ | $\nu 2 = 61.12$ |
| | | $R_3 = 214.715$ | | $S_2 = 20.17$ | | |
| | II | $R_4 = 105.05$ | $T_3 = 8.0$ | | $ND_3 = 1.589$ | $\nu 3 = 61.12$ |
| | | $R_5 = -178.20$ | | $S_3 = 0.10$ | | |
| | III | $R_6 = 187.62$ | $T_4 = 6.0$ | | $ND_4 = 1.589$ | $\nu 4 = 61.12$ |
| | | $R_7 = \infty$ | | $S_4 = 33.02$ | | |
| | IV | $R_8 = -106.00$ | $T_5 = 4.0$ | | $ND_5 = 1.589$ | $\nu 5 = 61.12$ |
| | | $R_9 = 106.00$ | | $S_5 = 18.85$ | | |
| | NORMAL IMAGE PLANE 2 | | | $S_6 = 11.77$ to $152.77$ | | |
| VARIABLE SPHERE | Mirror 5 | | | $S_7 = 41.00$ | | |
| | Mirror 6 | | | $S_8 = 17.23 + S_6$ | | |
| | Mirror 8 | | | $S_9 = 25.00$ | | |
| VARIABLE CYLINDER | V | $R_{10} = \infty$ | $T_6 = 5.0$ | | $ND_6 = 1.523$ | $\nu 6 = 58$ |
| | | $R_{11} = 261.5$ (Cyl) | | $S_{10} = 28.3$ to $139.4$ | | |
| | VI | $R_{12} = \infty$ | $T_7 = 5.0$ | | $ND_7 = 1.523$ | $\nu 7 = 58$ |
| | | $R_{13} = 174.33$ (Cyl) | | $S_{11} = 2.0$ | | |
| | VII | $R_{14} = \infty$ | $T_8 = 5.0$ | | $ND_8 = 1.617$ | $\nu 8 = 55.1$ |
| | | $R_{15} = 103$ | $T_9 = 5.0$ | | $ND_9 = 1.617$ | $\nu 9 = 36.6$ |
| | | $R_{16} = \infty$ | | $S_{12} = 160 - S_{10}$ | | |
| | VIII | $R_{17} = \infty$ | $T_{10} = 5.0$ | | $ND_{10} = 1.523$ | $\nu 10 = 58$ |
| | | $R_{18} = -348.67$ (Cyl) | | $S_{13} = 12.0$ | | |
| | | $R_{19} = 100.16$ | | | | |

TABLE I-continued (Test Optics)

| Function | Lens No. | Radius (R) | Thickness (T) | Spacing (S) | Refractive Index (ND) | Abbe Number (V) |
|---|---|---|---|---|---|---|
| COLLIMATOR | IX | $R_{20} = -71.456$ | $T_{11} = 10.0$ | | $ND_{11} = 1.523$ | $V_{11} = 58.6$ |
| | | $R_{21} = -344.10$ | $T_{12} = 5.0$ | | $ND_{12} = 1.617$ | $V_{12} = 36.6$ |
| | Mirror 11 | | | $S_{14} = 32.00$ | | |
| | | | | $S_{15} = 23.30$ | | |
| | X | $R_{22} = 111.275$ | $T_{13} = 5.0$ | | $ND_{13} = 1.589$ | $V_{13} = 61.12$ |
| | | $R_{23} = 59.570$ | | | | |
| | Mirror 12 | | | $S_{16} = 93.10$ | | |
| | TARGET | | | $S_{17} = 110.88$ | | |
| COLLECTOR | XI | $R_{24} = 40.356$ | $T_{14} = 5.0$ | $S_{18} = 18.5$ | $ND_{14} = 1.523$ | $V_{14} = 58.6$ |
| | | $R_{25} = \infty$ | | | | |
| | XII | $R_{26} = 40.356$ | $T_{15} = 5.0$ | $S_{19} = 6.0$ | $ND_{15} = 1.523$ | $V_{15} = 58.6$ |
| | | $R_{27} = \infty$ | | | | |
| | Blue Filter 15 | | $T_{16} = 3.0$ | $S_{20} = 39.30$ | | |
| | Diffuser (Flashed Opal) 14 | | $T_{17} = 3.0$ | | | |
| | | | | $S_{21} = 19.5$ | | |

It has been found most convenient to move the test instrument into proper position for testing an eye rather than to attempt to position the patient and/or his eye relative to the instrument. In connection therewith, co-pending application Ser. No. 773,572 filed Mar. 3, 1977, describes a mechanism suitable for supporting the instrument and conveniently permitting three-dimensional movement thereof for alignment purposes.

An alignment system which permits an operator to accurately position a member, such as eyepiece 4 shown in FIGS. 1, 2 and 4, in the chosen relationship to an object such as eye 1 is illustrated schematically in FIGS. 1 and 2.

A doctor's eye 100 sees an image of the patient's eye 1 at stationary lens CI, which is usually mounted in the instrument case (not shown). Lens CIII provides a zone of parallel light between it and lens CII in order that the image focus is not affected by an increase or decrease in the nominal distance between lenses CII and CIII. This not only permits small movement of the instrument within its case for alignment with the patient's eye, but also permits shifting the instrument a substantial distance (65 mm more or less) for the examination of both eyes without repositioning of a patient's head and without affecting the focus of the alignment system. The optical system is preferrably designed so that the distance of the eye 100 from lens CI is not critical. For example, the eye 100 may move through a range of 2-6 inches without significant effect. In addition, it is desirable to have lens CII of a substantially greater diameter than that of lens CIII in order that movement in a plane perpendicular to the observation axis does not result in cutting off the image or occluding a portion of the light transmitted through lens CIII toward lens CII. For example, lens CIII may have a diameter of 35 mm and lens CII may have a diameter of 54 mm. Lateral, horizontal and vertical positioning of eyepiece 4 relative to eye 1 is accomplished by positioning the image of eye 1 within a centering reticle located on plano surface 105 of lens CIV. The distance between eyepiece 4 and eye 1 is adjusted by means of a split-image range finder. The image of the eye is split horizontally and, when the upper and lower halves of the image of eye 1 mate at the line of separation, the spacing between eye 1 and eyepiece 4 is adjusted to the chosen distance. The split image is formed by a pair of observation axes 101 and 102 converging on eye 1 at respective horizontal angles 103 and 104 of 15 degrees to the left and right of the test axis respectively. Lenses CVa and CVb form an image of eye 1 at an image plane located on plano surface 105 of lens CIV. An assembly with mirrors 106, 107 and 108 redirect the observation axis 101 toward reflecting surface 109 of prism 110. Reflection by mirror 108 acts to rotate the image of eye 1 90 degrees in order that only the lower half of an image of eye 1 is presented to the image plane at lens surface 105 by reflecting surface 109. Similarly, mirrors 111, 112 and 113 redirect observation axis 102 toward reflecting surface 114 of prism 110. Reflection by mirror 112 acts to rotate the image of eye 1 90 degrees in order that only the upper half of an image of eye 1 is presented to the image plane at lens surface 105, by reflecting surface 114. The rotation of the image of eye 1 by mirrors 108 and 112 respectively, permits prism apex 115 of reflecting surfaces 109 and 114 to be vertical while permitting the conventional horizontal splitting of the image of eye 1. Mirror 116 deflects the combined observation axis to lens CII. Mirrors 117, 118 and 119 direct the observation axis to lens CI, while extending the distance between lenses CI and CII. Mirror 118 acts to rotate the entire image 90 degreees in order that the eye 100 may observe the image in a conventional horizontal split form. The number of mirrors between plano surface 105 and lens CV can be chosen to present an image with the left and right portions of the eye corresponding to the left and right portions of eye 1.

As with the preferred embodiment, it may be frequently desirable to present the image as a true replica, i.e. left on left, top on top, etc., but to have the image appear to move in the field in order that the image appears to move in the same relative direction as the control used to move the instrument although the field moves about the image. If a joystick, such as that shown in the aforementioned copending application, Ser. No. 773,572, is used to position the instrument, the instrument actually moves left when the joystick is moved right, down when the joystick moves up and vice versa; but, the image of the eye moves right in the field, when the joystick moves right, up when the joystick moves up and so on.

Specific parameters of a preferred optical system are set forth in Table II. The successive lens radii are designated $R_{101}$ to $R_{110a\&b}$, where a minus sign (−) signifies a surface curvature having a vertex on the eye 1 side of the lens; successive axial thicknesses are designated $T_{101}$ to $T_{105a\&b}$; successive axial spacings from eye 1 are designated $S_{101}$ to $S_{114a\&b}$, and all radii thicknesses and spacings are in millimeters. The refractive indices of the successive elements are designated $ND_{101}$ to $ND_{105a\&b}$, and Abbe numbers of the successive elements are designated $v101$ to $v105a\&b$. Abbe numbers and refractive indices are absolute values.

TABLE II
ALIGNMENT OPTICS

| Lens No. | Radius (R) | Thickness (T) | Spacing (S) | Refractive Index (ND) | Abbe Number (V) |
|---|---|---|---|---|---|
| CI | $R_{101} = -66.418$ | $T_{101} = 5.0$ | $S_{101} = 300-400$ | $ND_{101} = 1.523$ | $V101 = 58.6$ |
|  | $R_{102} = \infty$ |  |  |  |  |
|  | Mirror |  | $S_{102} = 26$ |  |  |
|  | Mirror |  | $S_{103} = 48$ |  |  |
|  | Mirror |  | $S_{104} = 46$ |  |  |
|  |  |  | $S_{105} = 30$ |  |  |
| CII | $R_{103} = \infty$ | $T_{102} = 7.0$ |  | $ND_{102} = 1.523$ | $V102 = 58.6$ |
|  | $R_{104} = 80.879$ |  |  |  |  |
|  |  |  | $S_{106} = 13$ to $97$ |  |  |
| CIII | $R_{105} = 80.879$ | $T_{103} = 5.0$ |  | $ND_{103} = 1.523$ | $V103 = 58.6$ |
|  | $R_{106} = \infty$ |  |  |  |  |
|  | Mirror |  | $S_{107} = 28$ |  |  |
|  |  |  | $S_{108} = 120$ |  |  |
| CIV | $R_{107} = 51.593$ | $T_{104} = 5.0$ |  | $ND_{104} = 1.523$ | $V104 = 58.6$ |
|  | $R_{108} = \infty$ (Reticle) |  |  |  |  |
|  | Prism |  | $S_{109} = 0.3$ |  |  |
|  | Mirror | $S_{110a} = 54.3$ | Mirror $S_{110b} = 78.3$ |  |  |
|  | Mirror | $S_{111a} = 48.0$ | Mirror $S_{111b} = 33.9$ |  |  |
|  | Mirror | $S_{112a} = 33.9$ | $S_{112b} = 48.0$ |  |  |
|  |  | $S_{113a} = 42.7$ | $S_{113b} = 18.7$ |  |  |
|  | $R_{109a\&b} = -93.584$ | $T_{105a\&b} = 5.0$ |  | $ND_{105a\&b} = 1.523$ | $V105a\&b = 58.6$ |
|  | $R_{110a\&b} = 93.584$ |  | $S_{114a\&b} = 179$ |  |  |

What is claimed is:

1. A subjective refractor for determining lens values required to correct visual deficiencies of an eye which comprises,
   a target, means to project an image of said target to a normal image plane on a test axis,
   first reflection means to axially move said target image to either side of said normal image plane,
   second and third reflection means to fold the test axis,
   an axially-rotatable cylinder means to axially move one meridian of said target image to either side of said image, said cylinder means being located between said second and third reflection means, and
   an eyepiece having a front focal plane located at a position up to 4 mm from said normal image plane whereby any single exterior dimension of said instrument is substantially less than the test axis distance between said target and said eyepiece.

2. The subjective refractor of claim 1 wherein said first reflection means comprises first and second mirrors and a first portion of the test axis between said second mirror and said second reflection means is parallel to a second portion of the test axis between said eyepiece and said first mirror.

3. The subjective refractor of claim 1 wherein the first reflection means is a single mirror having a reflective surface normal to said test axis and said second reflection means is a semitransmissive mirror, located on the test axis between said first reflection means and said eyepiece.

4. The subjective refractor of claim 1 wherein said third reflection means comprises third and fourth mirrors, the test axis between said target and said second reflection means is in a single plane and a fourth portion of the test axis between said target and said fourth mirror is parallel to a third portion of the test axis between said third mirror and said second reflection means.

5. The subjective refractor of claim 2 wherein said third reflection means comprises third and fourth mirrors, the test axis between said target and said second reflection means is in a single plane and a fourth portion of the test axis between said target and said fourth mirror is parallel to a third portion of the test axis between said third mirror and said second reflection means.

6. The subjective refractor of claim 5 further including first and second collimating lenses, said third mirror being located between said collimating lenses.

7. The subjective refractor of claim 6 wherein the normal image plane is spaced toward said eyepiece 1.16 mm from the focal plane of said eyepiece.

8. The subjective refractor of claim 6 having the following parameters; where radii are in millimeters and are identified as $R_1$ to $R_{27}$, a minus sign (−) signifying the vertex of the surface lies on the eye 1 side of the lens; thicknesses are millimeters and are identified as $T_1$ to $T_{17}$; spacings are in millimeters and are identified as $S_1$ to $S_{21}$; indicies of refraction are identified as $ND_1$ to $ND_{15}$; Abbe numbers are identified as $v1$ to $v15$; and indicies of refraction and Abbe numbers are absolute values

| Function | Lens No. | Radius (R) | Thickness (T) | Spacing (S) | Refractive Index (ND) | Abbe Number (V) |
|---|---|---|---|---|---|---|
| | | | | $S_1 = -116.79$ | | |
| | | $R_1 = 134.30$ | $T_1 = 7.0$ | | $ND_1 = 1.784$ | $\sqrt{1} = 25.16$ |
| | I | $R_2 = 50.27$ | $T_2 = 10.0$ | | $ND_2 = 1.589$ | $\sqrt{2} = 61.12$ |
| | | $R_3 = 214.715$ | | $S_2 = 20.17$ | | |
| | | $R_4 = 105.05$ | | | | |
| | II | | $T_3 = 8.0$ | | $ND_3 = 1.589$ | $\sqrt{3} = 61.12$ |
| | | $R_5 = 178.20$ | | $S_3 = 0.10$ | | |
| | | $R_6 = 187.62$ | | | | |
| | III | $R_7 = \infty$ | $T_4 = 6.0$ | | $ND_4 = 1.589$ | $\sqrt{4} = 61.12$ |
| | | | | $S_4 = 33.02$ | | |
| | | $R_8 = -106.00$ | | | | |
| | IV | $R_9 = 106.00$ | $T_5 = 4.0$ | | $ND_5 = 1.589$ | $\sqrt{5} = 61.12$ |
| | | | | $S_5 = 18.85$ | | |
| | NORMAL IMAGE PLANE 2 | | | $S_6 = 11.77$ to $152.77$ | | |
| VARIABLE SPHERE | Mirror 5 | | | $S_7 = 41.00$ | | |
| | Mirror 6 | | | $S_8 = 17.23 + S_6$ | | |
| | Mirror 8 | | | $S_9 = 25.00$ | | |
| | V | $R_{10} = 28$ | $T_6 = 5.0$ | | $ND_6 = 1.523$ | $\sqrt{6} = 58$ |
| | | $R_{11} = 261.5$ (Cyl) | | $S_{10} = 28.3$ to $139.4$ | | |
| | VI | $R_{12} = \infty$ | $T_7 = 5.0$ | | $ND_7 = 1.523$ | $\sqrt{7} = 58$ |
| | | $R_{13} = -174.33$ (Cyl) | | $S_{11} = 2.0$ | | |
| | VII | $R_{14} = \infty$ | $T_8 = 5.0$ | | $ND_8 = 1.617$ | $\sqrt{8} = 55.1$ |
| | | $R_{15} = -103$ | $T_9 = 5.0$ | | $ND_9 = 1.617$ | $\sqrt{9} = 36.6$ |
| | | $R_{16} = \infty$ | | $S_{12} = 160-S_{10}$ | | |
| | VIII | $R_{17} = \infty$ | $T_{10} = 5.0$ | | $ND_{10} = 1.523$ | $\sqrt{10} = 58$ |
| | | $R_{18} = -348.67$ (Cyl) | | $S_{13} = 12.0$ | | |
| | | $R_{19} = 100.16$ | $T_{11} = 10.0$ | | $ND_{11} = 1.523$ | $\sqrt{11} = 58.6$ |
| | IX | $R_{20} = 71.456$ | $T_{12} = 5.0$ | | $ND_{12} = 1.617$ | $\sqrt{12} = 36.6$ |
| | | $R_{21} = 344.10$ | | $S_{14} = 32.00$ | | |
| | Mirror 11 | | | $S_{15} = 23.30$ | | |
| | | $R_{22} = 111.275$ | | | | |
| | X | $R_{23} = 59.570$ | $T_{13} = 5.0$ | | $ND_{13} = 1.589$ | $\sqrt{13} = 61.12$ |
| | | | | $S_{16} = 93.10$ | | |
| | Mirror 12 | | | $S_{17} = 110.88$ | | |
| | TARGET | | | $S_{18} = 0$ $18.5$ | | |
| | XI | $R_{24} = 40.356$ | $T_{14} = 5.0$ | | $ND_{14} = 1.523$ | $\sqrt{14} = 58.6$ |

-continued

| Function | Lens No. | Radius (R) | Thickness (T) | Spacing (S) | Refractive Index (ND) | Abbe Number (V) |
|---|---|---|---|---|---|---|
| COLLECTOR | XII | $R_{25} = \infty$<br>$R_{26} = 40.356$<br>$R_{27} = \infty$ | $T_{15} = 5.0$ | $S_{19} = 5.0$<br>$S_{20} = 39.30$ | $ND_{15} = 1.523$ | $V_{15} = 58.6$ |
| | Blue Filter 15 | | $T_{16} = 3.0$ | | | |
| | Diffuser (Flashed Opal) 14 | | $T_{17} = 3.0$ | $S_{21} = 19.5$ | | |

* * * * *

UNITED STATES PATENT AND TRADEMARK OFFICE
CERTIFICATE OF CORRECTION

PATENT NO. : 4,179,196

DATED : December 18, 1979

INVENTOR(S) : Persson et al.

It is certified that error appears in the above-identified patent and that said Letters Patent are hereby corrected as shown below:

In Table I:
Delete "$R_3 = 214.715$" and insert --$R_3 = -214.715$--.
Delete "$R_{13} = 174.33(Cyl)$" and insert --$R_{13} = -174.33(Cyl)$--.
Delete "$R_{15} = 103$" and insert --$R_{15} = -103$--.
Delete "$S_{19} = 6.0$" and insert --$S_{19} = 5.0$--.

In Table II:
Delete "$R_{105} = 80.879$" and insert --$R_{105} = -80.879$--.
Delete "$R_{107} = 51.593$" and insert --$R_{107} = -51.593$--.

In Claim 8:
Delete "$R_3 = 214.715$" and insert --$R_3 = -214.715$--.
Delete "$R_5 = 178.20$" and insert --$R_5 = -178.20$--.
Delete "$R_{10} = 28$" and insert --$R_{10} = \infty$--.
Delete "$R_{11} = 261.5(Cyl)$" and insert --$R_{11} = -261.5(Cyl)$--.
Delete "$R_{20} = 71.456$" and insert --$R_{20} = -71.456$--.
Delete "$R_{21} = 344.10$" and insert --$R_{21} = -344.10$--.
Delete "$S_{18} = 0\ 18.5$" and insert --$S_{18} = 18.5$--.

Signed and Sealed this

Fifteenth Day of September 1981

[SEAL]

Attest:

GERALD J. MOSSINGHOFF

Attesting Officer    Commissioner of Patents and Trademarks